(12) United States Patent
Bourne

(10) Patent No.: US 11,964,173 B2
(45) Date of Patent: Apr. 23, 2024

(54) RADIOTHERAPY DEVICE

(71) Applicant: Elekta Limited, Crawley (GB)

(72) Inventor: Duncan Bourne, Sussex (GB)

(73) Assignee: Elekta Limited, Crawley (GB)

( * ) Notice: Subject to any disclaimer, the term of this patent is extended or adjusted under 35 U.S.C. 154(b) by 328 days.

(21) Appl. No.: 16/946,877

(22) Filed: Jul. 9, 2020

(65) Prior Publication Data
US 2021/0016112 A1  Jan. 21, 2021

(51) Int. Cl.
*A61N 5/10* (2006.01)

(52) U.S. Cl.
CPC .................................. *A61N 5/1081* (2013.01)

(58) Field of Classification Search
CPC .. A61N 5/1081; A61N 5/1082; A61N 5/1083; A61B 6/4441; A61B 6/4447; A61B 2034/732
See application file for complete search history.

(56) References Cited

U.S. PATENT DOCUMENTS

| 6,182,582 | B1 * | 2/2001 | Bailey | B64G 1/22 |
| | | | | 108/22 |
| 7,729,473 | B2 * | 6/2010 | Jaffray | A61N 5/1084 |
| | | | | 378/65 |
| 8,151,660 | B2 * | 4/2012 | Wood | B23Q 1/5406 |
| | | | | 74/55 |
| 10,646,730 | B2 * | 5/2020 | Nord | A61N 5/1048 |
| 10,773,102 | B2 | 9/2020 | Allen et al. | |
| 11,126,063 | B2 * | 9/2021 | Meissner | G02F 1/3551 |
| 2009/0168961 | A1 | 7/2009 | Hieronimi et al. | |
| 2013/0158382 | A1 | 6/2013 | Chao | |
| 2019/0001158 | A1 | 1/2019 | Bergfjord et al. | |

FOREIGN PATENT DOCUMENTS

| CN | 107362464 A | 11/2017 |
| DE | 10161152 A1 | 6/2003 |
| EP | 1698191 A1 | 9/2006 |
| EP | 3527138 A2 | 8/2019 |
| GB | 2537120 A | 10/2016 |
| WO | WO-2008055517 A1 | 5/2008 |

OTHER PUBLICATIONS

"United Kingdom Application Serial No. 1909860.7, Examination Report dated Sep. 20, 2021", (dated Sep. 20, 2021), 2 pgs.
"Great Britain Application No. 1909860.7, Search and Examination Report dated Dec. 20, 2019", (dated Dec. 20, 2019), 7 pgs.

* cited by examiner

*Primary Examiner* — Thaddeus B Cox
*Assistant Examiner* — Joshua Daryl D Lannu
(74) *Attorney, Agent, or Firm* — Schwegman Lundberg & Woessner, P.A.

(57) ABSTRACT

Disclosed herein is a radiotherapy apparatus for delivering radiation to a patient. The apparatus comprises a gantry, a source of radiation attached to the gantry and configured to emit radiation along a radiation axis, a support structure for supporting the gantry, and a gantry rotation mechanism positioned between the support structure and the gantry. The gantry rotation mechanism is configured to rotate the gantry about a gantry rotation axis, and tilt the gantry with respect to the gantry rotation axis such that the radiation axis is non-perpendicular with the gantry rotation axis.

13 Claims, 8 Drawing Sheets

RADIOTHERAPY DEVICE

CLAIM FOR PRIORITY

This application claims the benefit of priority of United Kingdom Application No. 1909860.7, filed Jul. 19, 2019. which is hereby incorporated by reference in its entirety.

TECHNICAL FIELD

This disclosure relates generally to radiotherapy apparatuses and devices, and in particular relates to a radiotherapy apparatus for delivering radiation to a patient.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour. However, in order to apply a prescribed dose to a tumour or other target region within a subject, the radiation must pass through healthy tissue, irradiating and hence potentially damaging it in the process. Modem radiotherapy treatments provide a safe and relatively small radiation dose to healthy tissue, however it is desirable to minimise the dose received by healthy tissue still further during radiotherapy treatments.

Many different radiotherapy techniques exist, allowing radiation to be applied from different angles, at varying intensities, and for varying time periods. A standard approach to minimising the radiation dose received by healthy tissue surrounding a target region is to direct the radiation toward the target region from a plurality of different angles. This may comprise using different sources of radiation arranged at different angles around the patient, or may comprise rotating a source of radiation around the patient. In either case, each beam of radiation passes through the target region, and therefore a prescribed dose may be built up at the target region. However, importantly, applying the radiation beams at different angles means that the radiation dose applied to healthy tissue is spread over a larger region of healthy tissue, thus reducing the dose received by one particular unit volume of healthy tissue.

An example prior art radiotherapy apparatus is shown in FIGS. 1a and 1b. The figures show a cross-section through a radiotherapy device 120 comprising a radiation source 100 and a detector 102 attached to a gantry 104, the gantry comprising a circular support track 106 such that the radiation source 100 and detector 102 are arranged diametrically opposed to one another. FIGS. 1a and 1b also show a patient 108 lying on a patient support surface 110. As the radiation is delivered to the patient, for example according to a treatment plan, the to radiation source 100 and the detector 102 rotate together around the circular support track 106 such that they are always arranged 180° from one another around the gantry 104. The radiation source 100 directs radiation toward the patient 108 from various angles around the patient 108 in order to spread out the radiation dose received by heathy tissue to a larger region of healthy tissue while building up a prescribed dose of radiation at a target region. In FIG. 1a, the radiation source 100 is at the top of the circular support track 106 and the detector 102 is at the bottom of the circular support track 106. FIG. 1b shows both components having been rotated 180° around the circular support track 106. While this apparatus allows the radiation dose applied to healthy tissue to be reduced when compared to a treatment in which radiation is applied at a single angle, it will be appreciated that once the radiation source 100 has been rotated through 180° around the circular support track 106, any subsequent radiation beams begin to pass through regions of healthy tissue which have already been irradiated. This increases the radiation dose applied to healthy tissue.

The device depicted in FIGS. 1a and 1b is a co-planar device configured to provide co-planar radiotherapy treatment. Radiation is emitted in a plane which is perpendicular to the axis of rotation of the radiation source 100. In devices such as those depicted in FIG. 1, radiation may be delivered to a radiation isocentre 112 at the centre of the gantry 104 regardless of the angle to which the radiation head is rotated around the gantry 104. However, the volume of healthy tissue available in which to spread the radiation dose is relatively small, thus imposing restrictions on the treatment which can be provided by such devices.

Radiotherapy apparatuses and devices which allow non-coplanar treatment also exist. Noncoplanar devices allow radiation to be emitted at an angle to the radiation source rotation axis. Typically, such devices have radiation sources configured to emit radiation outside the gantry plane. An example of this type of device is depicted in FIGS. 2a and 2b, where like reference numerals as used with respect to figures la and 1b have been used to depict like components. In the radiotherapy device 220 of FIGS. 2a and 2b, the radiation source 200 is rotatably attached to the gantry 204, allowing it to pivot and thus to provide radiation outside the plane of the gantry 204. FIG. 2a shows the radiation source at an uppermost point of the gantry 204, directing radiation out of the plane of the gantry 204 and down toward a patient 208. FIG. 2b is the same radiotherapy device 220 after the radiation source 200 has been rotated 180° to direct radiation up toward a patient from a lowermost point of the gantry. In non-coplanar devices such as the radiotherapy device 220 depicted in FIGS. 2a and 2b, emitted radiation sweeps out a cone shape as the radiation source 200 is rotated, with the radiation isocentre 212 being at the tip of the cone. Different cone angles can be achieved by pivoting the radiation source 200 about the gantry 204. Such radiotherapy devices have the benefit of allowing the radiation dose to be spread throughout a larger area of healthy tissue, and in particular for a given 'angle of tilt' of the radiation source, i.e. for a given 'cone angle', radiation may be directed through a different region of healthy tissue as the radiation source 200 is rotated 360° around the patient. Consequently, the radiation dose received by any one unit volume of healthy tissue may be reduced in comparison with co-planar treatment. However, pivoting the radiation source 200 with respect to the gantry 204 changes the position of the radiation isocentre 212, and for certain radiotherapy procedures this may mean having to move the relative positions of the gantry 204 and the patient 208 in order to ensure that radiation continues to pass through the target region. This requires expensive and space-consuming actuating mechanisms which either move the patient support surface 210, move the gantry 204 along the horizontal rotation axis, or both. Making use of these actuating mechanisms also typically increases the duration of the treatment, which is not desirable. Another disadvantage arises because the radiation is being applied outside the gantry 204 plane and at varying angles, and it is therefore difficult to incorporate a detector or a beam stop into the apparatus. Again, additional complex and expensive actuation mechanisms may be required in order to position a detector or beam stop 202 in the path of the radiation beam after it has exited the patient 208, and to adjust the position of the detector or beam stop 202 as the radiation source 200 is pivoted/rotated with respect to the gantry 204. Alternatively, a large amount of shielding must be placed around the radiotherapy device 220 in order to halt the beam and thus provide a safe environment around the radiotherapy device 220.

The present invention seeks to address these and other disadvantages encountered in the prior art by providing an improved radiotherapy device.

SUMMARY

An invention is set out in the independent claims, and optional features are set out in the dependent claims.

FIGURES

Specific embodiments are now described, by way of example only, with reference to the drawings, in which.

Figure 3A:
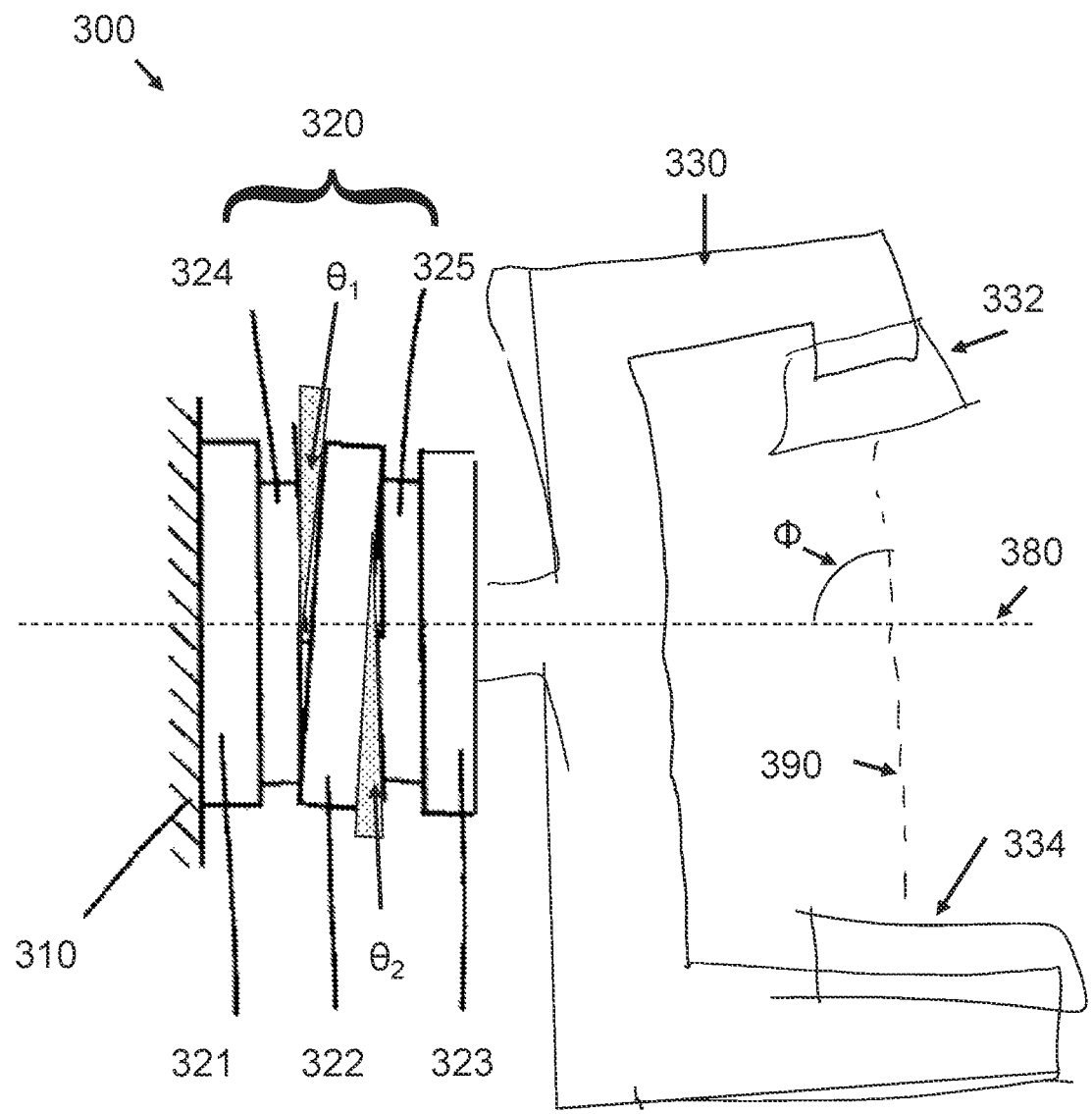
Figure 3B:
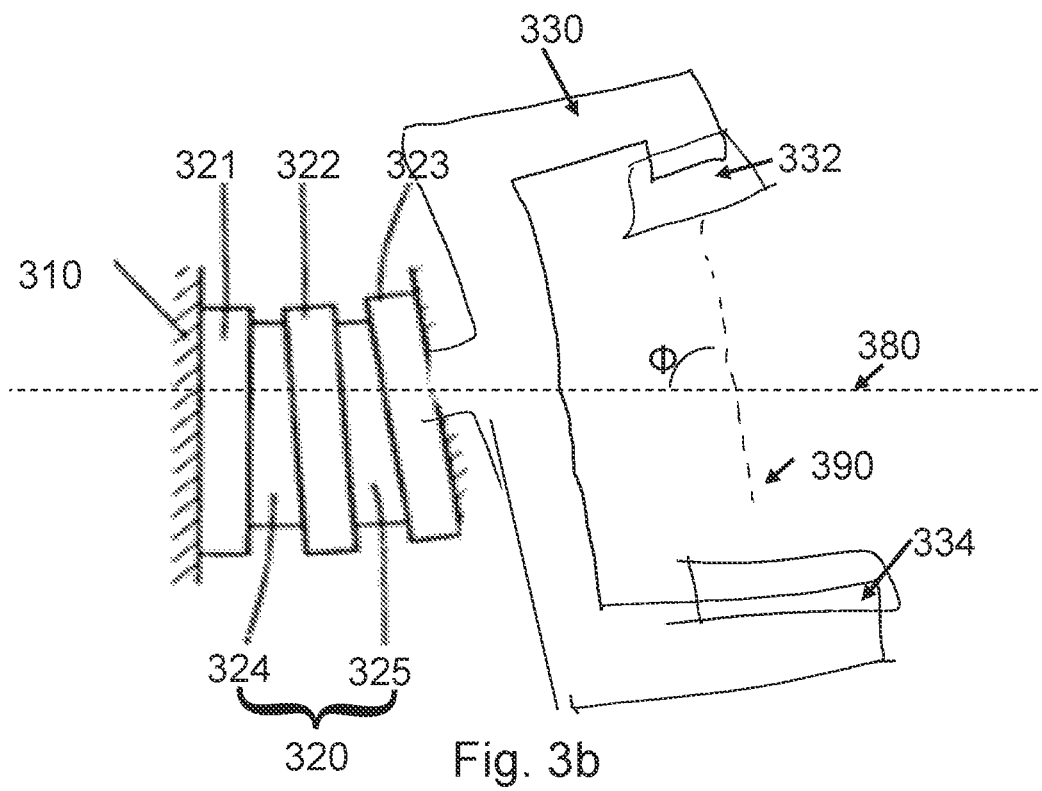
Figure 3C:
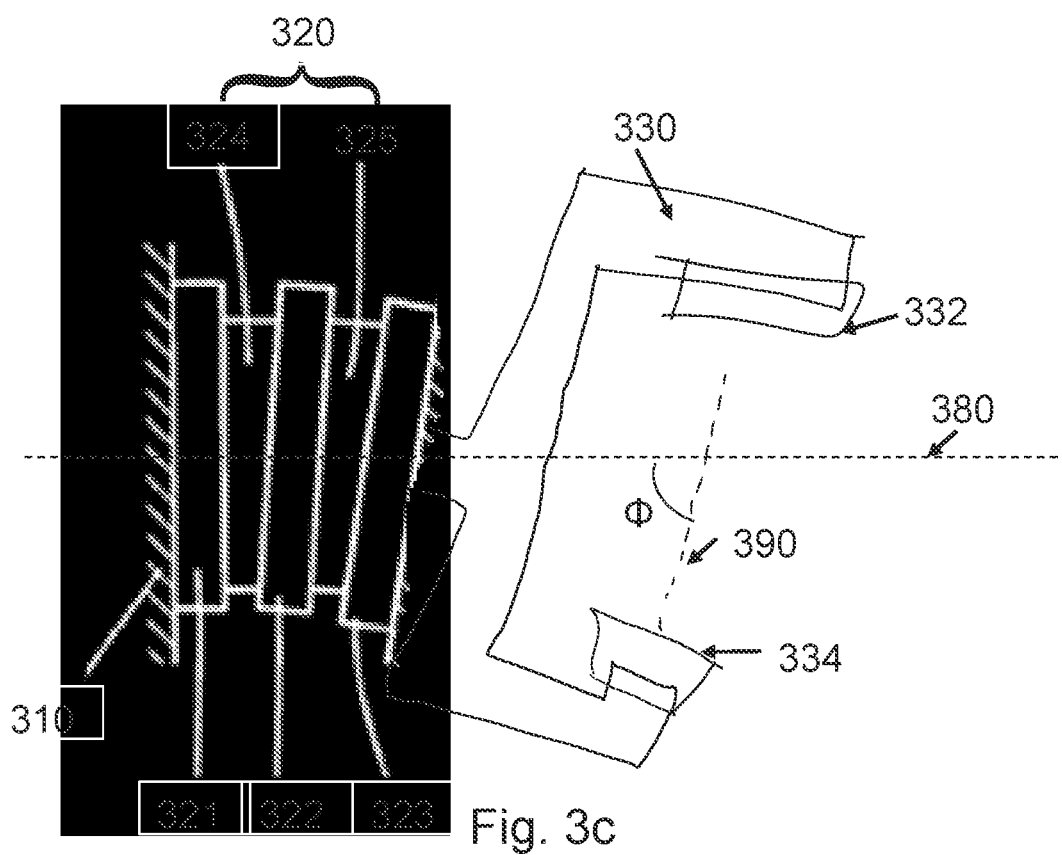
Figure 4A:
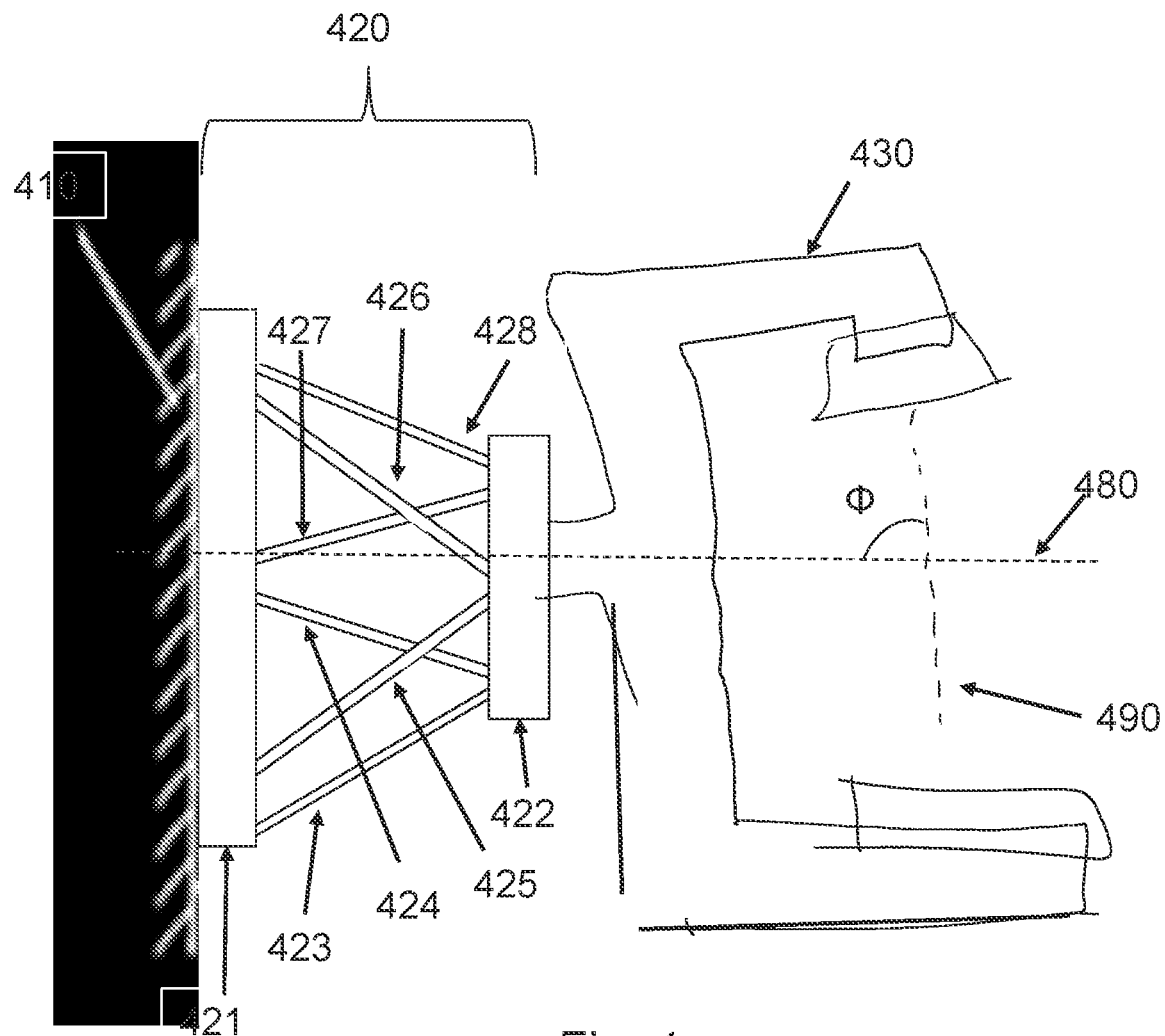
Figure 4B:
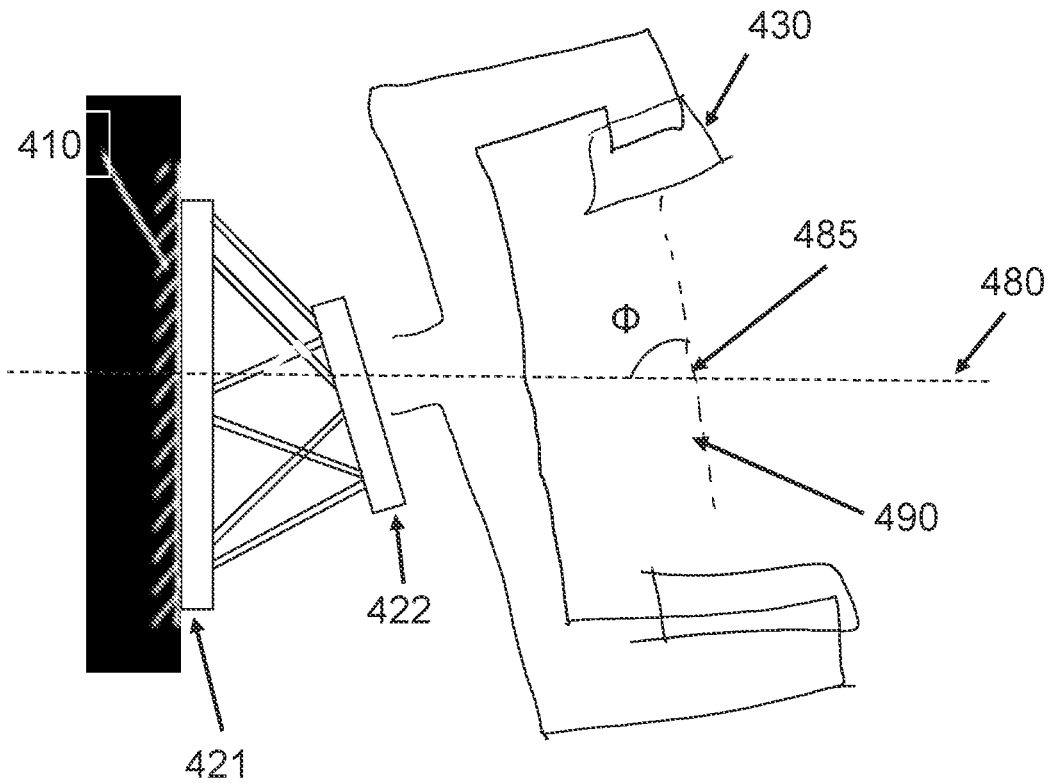
Figure 4C:
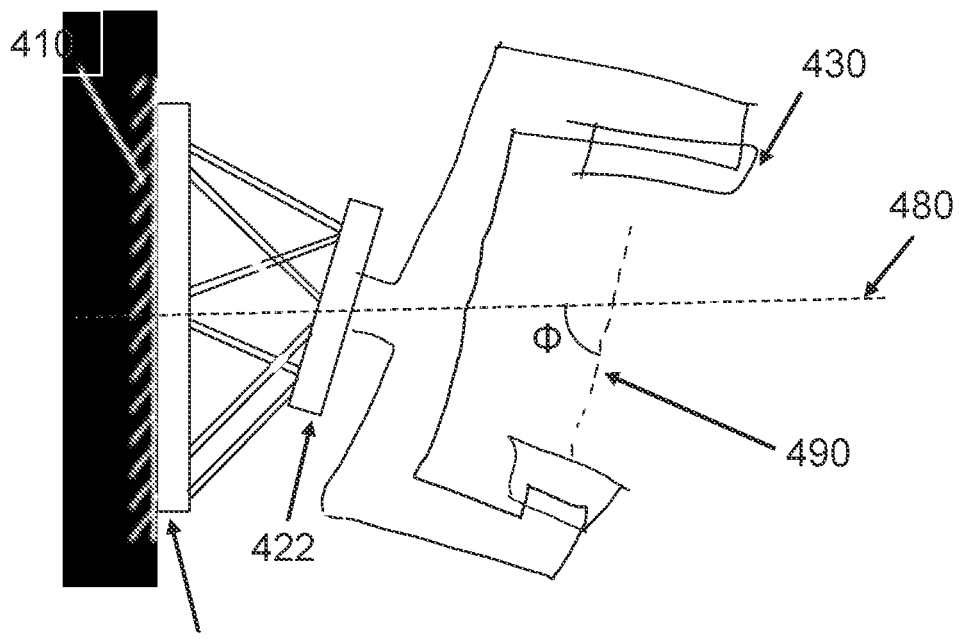

FIGS. 3a-c depict a radiotherapy apparatus according to a first embodiment of the present disclosure;

FIGS. 4a-c depict a radiotherapy apparatus according to a second embodiment of the present disclosure; and FIGS. 5a-d depict a radiotherapy apparatus according to a third embodiment of the present disclosure.

Figure 6:
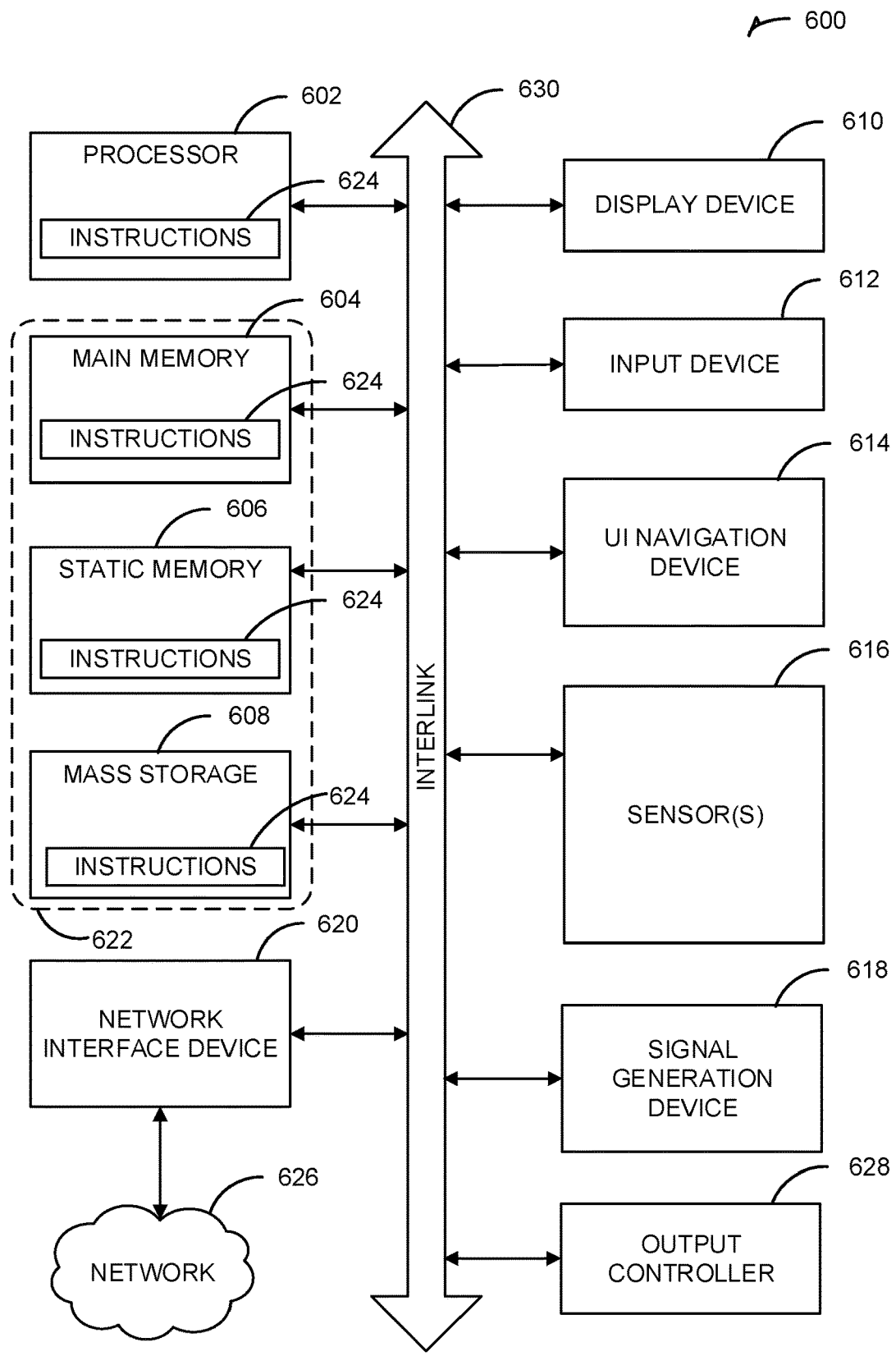

FIG. 6 depicts a block diagram illustrating an example of a machine upon which one or more embodiments may be implemented

DETAILED DESCRIPTION

FIGS. 3a-c depict a radiation treatment apparatus according to the present disclosure. The apparatus is suitable for and configured to direct radiation toward a patient, for example according to a radiotherapy treatment plan. The apparatus comprises a gantry 330, a support structure 310 for supporting the gantry 330, a source of radiation 332 attached to the gantry 330, and a gantry rotation mechanism 320.

The radiation source 332 is configured to provide therapeutic radiation to a patient. The radiation source 332 may be any of a number of different types of radiation sources known to the skilled person, for example a kilovoltage therapy x-ray unit or a linear accelerator (LINAC). A LINAC suitable for use in radiotherapy, e.g. a clinical LINAC, comprises a number of components not shown in the figures, for example an electron gun, a source of RF energy such as a magnetron, a waveguide in which the electrons are accelerated toward a target, and a heavy metal target configured to convert energetic electrons into X-rays in a known manner and hence produce radiation. A clinical LINAC may also comprise a treatment head comprising a collimator, beam-shaping apparatus and dosimetry apparatus.

The radiation apparatus may also further comprise a radiation detector 334. The radiation to detector 334 may be any suitable radiation detector and may comprise imaging means, i.e. imaging apparatus or an imaging device, to allow imaging of the patient. For example, the imaging device may comprise a portal imaging detector. For electronic portal imaging, an electronic portal imaging device (EPID) is placed in the path of the treatment beam such that radiation can he emitted from the radiation source 332 along a radiation axis 390 or beam path, through a patient, and be incident on the EPID. The detector 334 allows radiotherapists to plan image guided radiotherapy treatments according to known techniques.

Figure 1A:
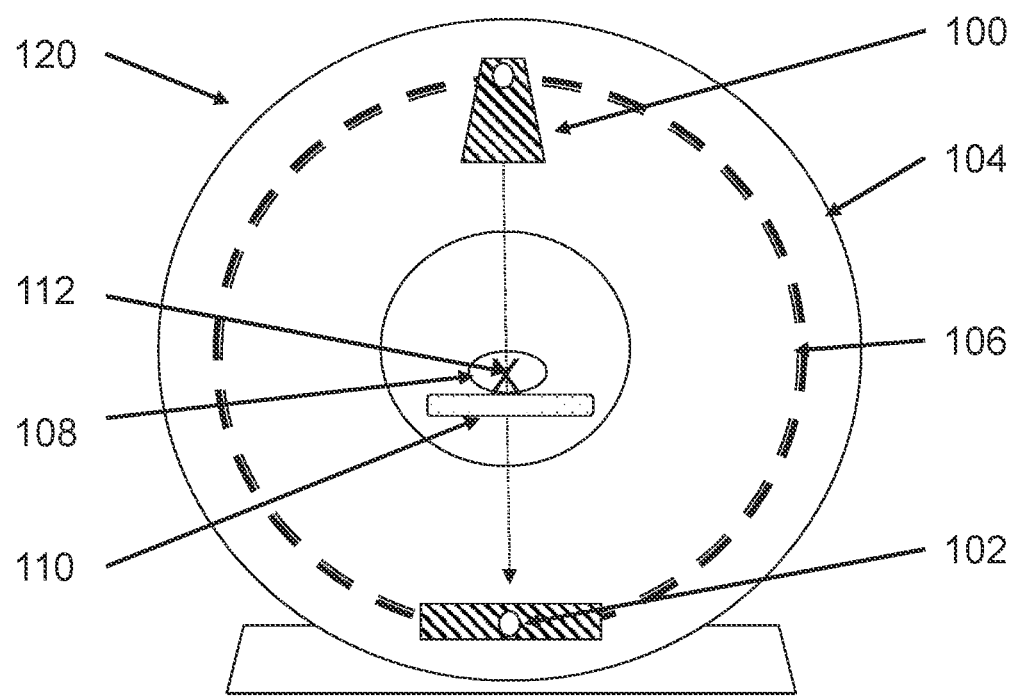
FIGS. 1a and 1b depict a radiotherapy apparatus according to the prior art which is suitable for providing coplanar treatment.
Figure 1B:
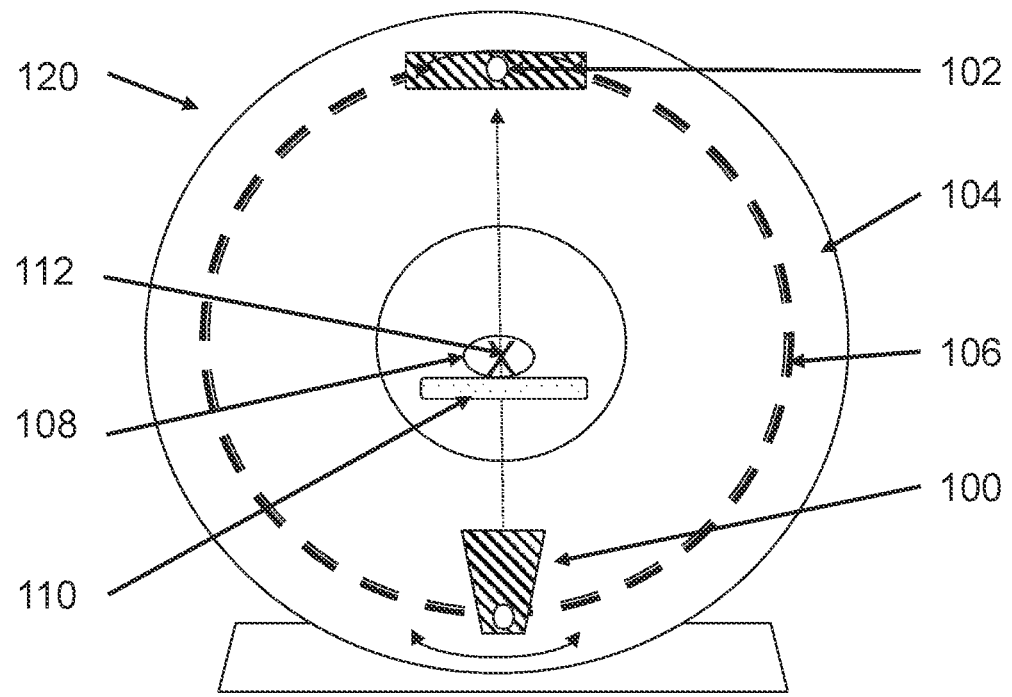
Figure 2A:
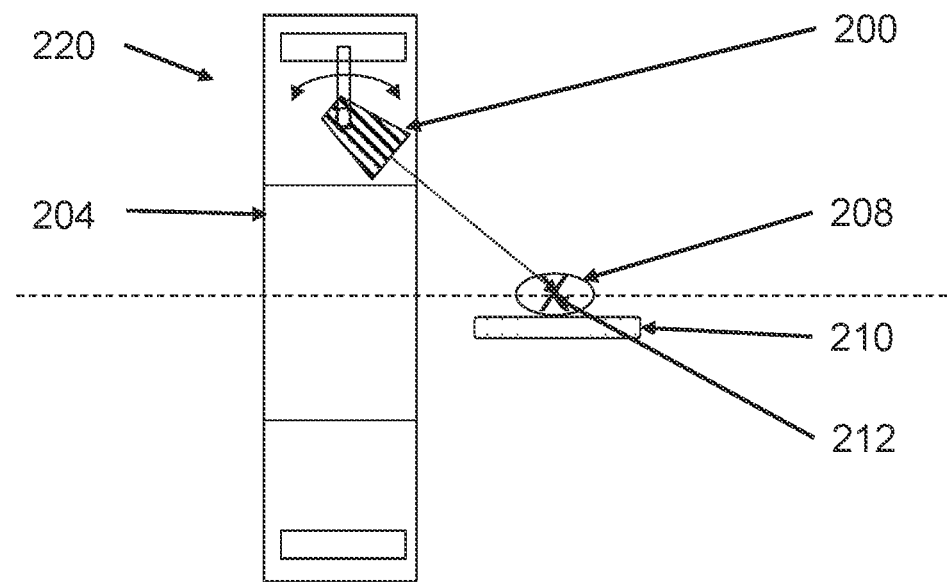
FIGS. 2a and 2b depict a radiotherapy apparatus according to the prior art which is suitable for providing non-coplanar treatment.
Figure 2B:
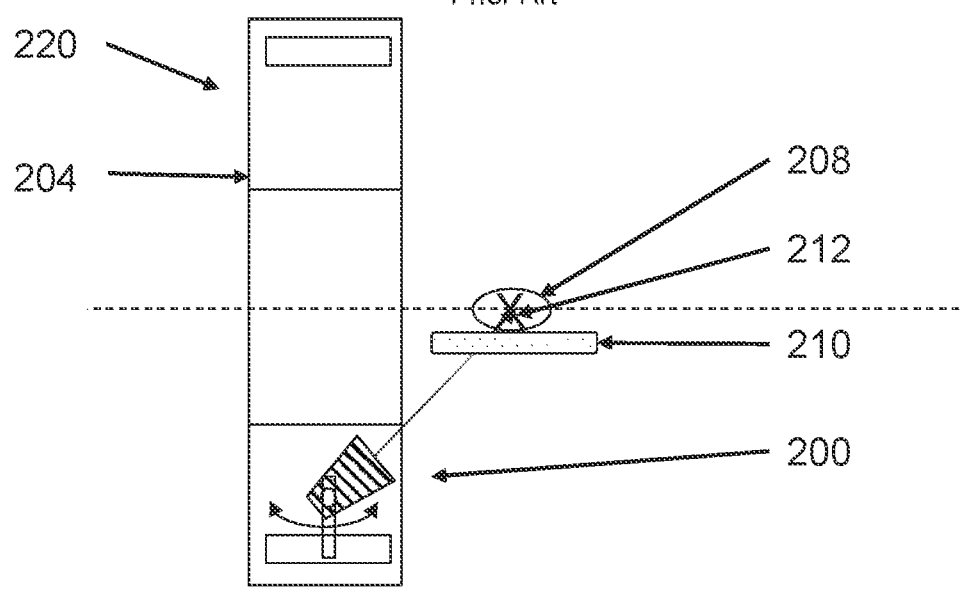

The radiation apparatus 300 further comprises a gantry 330. The gantry 330 shown in the figures is a C-arm gantry, though a ring-type gantry similar in type to the gantries depicted in FIGS. 1 and 2 may be used with the apparatuses of the present disclosure. The radiation source 332 and detector 334 are both attached to the gantry 330. The c-arm shown in FIGS. 3a-c has two opposing cantilevered arms, with the radiation source 332 and detector 334 attached to a respective one of the arms. In a preferred implementation, the radiation source 332 and detector 334 are positioned diametrically opposite one another and are fixedly attached to the gantry 330 such that they cannot rotate with respect to the gantry 330. This means that, as the gantry is rotated about axis 380 in a manner to be detailed below, the relative positions of the radiation source 332 and detector 334 do not change. In other words, the radiation source 332 is configured to direct radiation toward the detector 334 and this is not affected as the gantry is rotated and/or tilted. This fixed orientation of the radiation source 332 and detector 334 ensures that the patient can be imaged no matter the tilt or rotation angle of the gantry 330, and no complex and expensive actuating mechanisms are required to adjust the position of either the radiation source 332 or the detector 334 in the manner required by some devices in the prior art. Alternatively, a beam stop can be placed opposite the radiation source 332. This is advantageous for similar reasons; as the radiation source 332 is always positioned opposite the beam stop and as the radiation axis 390 passes through the beam stop no matter the orientation of the gantry 330, effective shielding is provided in a simple manner without expensive and complex actuating mechanisms.

The radiotherapy apparatus also comprises a bore. Typically, the bore of a radiotherapy device is cylindrical. A patient support surface is positioned in the bore such that radiation can be directed toward a patient positioned on the support surface. The bore of the apparatus can be formed by a framework, which may otherwise be described as a chassis, a shielding structure, a shell, or a casing. The framework defines the outer surface of the device which to the patient sees upon entering the treatment room, as well as defining the inner surface of the bore which the patient sees when positioned inside the bore. The framework also defines a hollow region of annular cross-section in which the gantry 330 can be both rotated and tilted in the manner described herein. Thus, the patient is shielded from the rotatable gantry 330. Movement of the gantry 330 is hidden from the patient's view, reducing intimidation and distress which may otherwise be caused if the patient were able to see rotation of the large gantry 330, and also reducing the likelihood that the patient can accidentally touch or otherwise interfere with the movement of the gantry 330. This means that the gantry 330 can be rotated quickly, efficiently and safely.

The apparatus 300 further comprises a support structure 310 which supports the gantry 330. The support structure 310 supports both the gantry rotation mechanism and the gantry. The support structure 310 may be a frame or any other structure which is able to support the weight of the gantry 330. The support structure 310 may be, for example, a wall. In a preferred implementation, the support structure 310 comprises a surface defining a plane to Which the gantry rotation mechanism 320 can attach and which is perpendicular to a gantry rotation axis 380. As will be described herein, the gantry rotation axis 380 may be described as a fixed axis, i.e. the gantry is rotated about this axis no matter its tilt angle. The gantry rotation axis is 'fixed'. The orientation and position of the axis may be fixed with respect to the support surface.

The apparatus further comprises a gantry rotation mechanism 320. The gantry rotation mechanism 320 is configured to rotate the gantry 330 about a fixed axis 380 which passes through the gantry rotation mechanism 320, and is also configured to tilt the gantry 330 with respect to the fixed axis 380. The gantry may be tilted such that the radiation axis 390 is non-perpendicular with the gantry rotation axis 380. The gantry rotation mechanism 320 can take multiple forms, for example an embodiment in which rotatable wedges are used to impart a tilt angle to the gantry 330 (as shown in FIGS. 3a-c). Alternatively, the gantry rotation mechanism may comprise a Stewart platform, otherwise known as a hexapod. Still further, the gantry rotation mechanism 320 may comprise one or more wedge shapes which can dynamically adjust their wedge angle, and hence the tilt angle of the gantry, using pistons or the like. Still further, the gantry rotation mechanism may comprise a single wedge element or static wedge which has a wedge angle such that the gantry is permanently tilted with respect to the gantry rotation axis 380.

FIG. 3a-c shows a radiation treatment apparatus 300 comprising a first embodiment of the gantry rotation mechanism 320. In the first embodiment, the mechanism comprises three rotary actuators 321, 322, 323 with a first wedge 324 positioned between the first 321 and second 322 rotary actuators and a second wedge 325 positioned between the second 322 and third 323 rotary actuators. The first 321, second 322 and third 323 rotary actuators are configured to cause a relative rotation between their opposing faces about a first, a second and a third rotation axis respectively. The wedges act to bring the three rotation axes of the rotary actuators in and out of alignment. The rotary actuators may be described as rotation means, means for effecting rotation, rotators, or actuators comprising rotatable elements. FIG. 3a shows the gantry rotation mechanism 320 in its "zero tilt" state, i.e. in which the axes of the three rotary actuators are aligned. FIG. 3b shows the apparatus at its maximum angular displacement in a first tilt direction, while FIG. 3c shows the apparatus at its maximum angular displacement in a second, opposing tilt direction.

The first rotary actuator 321 is supported directly on the support structure 310. The rotary actuator 321 is configured to rotate its 'inner' face by a selected angle or a selected angular rate relative to its 'outer' face. The outer face may form a stator face and the inner face may comprise or be formed of a rotatable element or rotor. The inner face of the first rotary actuator 321 may be described as the face which faces the gantry 330, while the outer face can be described as the face which faces the support structure 310. The first rotary actuator 321 may be cylindrical, or substantially cylindrical. Mounted to the inner face of the first rotary actuator 321 is a wedge 324, which is generally cylindrical or disc-shaped, but has an inner face which is non-parallel to its outer face. This shape is referred to as a cylindrical wedge. The inner face of the first rotary actuator 321 forms an angle $\theta_1$ with the outer face of the first rotary actuator. Mounted to the top of the first wedge 324, there is a second rotary actuator 322. The second rotary actuator 322 is also configured to rotate its inner face with respect to its outer face and is preferably cylindrical. The second rotary actuator 321 may be identical in form and function to the first rotary actuator 321. Mounted to the inner, i.e. gantry-facing, face of the second rotary actuator 322 is a second wedge 325 which, like the first wedge 324, has non-parallel inner and outer faces. The angle formed between the inner and outer faces of the second wedge 325 is $\theta_2$. Mounted to the inner, gantry-facing face of the second wedge 325 is a third rotary actuator 323. The third rotary actuator 323 may be of the same form as the first and second rotary actuators 321, 322. The outer face of the first rotary actuator 321 may be described as the outer, or support surface-facing, face of the rotation mechanism 320, and the inner face of the third rotary actuator 333 may be described as the inner, or gantry-facing, face of the rotation mechanism 320. The gantry rotation mechanism 320 is configured to alter, i.e. adjust, the angle which its inner face makes with its outer face.

The gantry 330 is coupled to the inner face of the third rotary actuator 323. Alternatively, the inner face of the third rotary actuator 323 may be integral with the third rotary actuator 323. In either case, the gantry 330 rotates with the inner face of the third rotary actuator 323. In other words, there is no relative rotation between the third rotary actuator 323 inner face and the gantry 330.

The first rotary actuator 321 is configured to rotate the gantry 330 about a gantry rotation axis 380 which is fixed with respect to the support surface 310 and first rotary actuator 321 and may thus be called a fixed axis 380. The fixed axis 380 may be a horizontal axis, i.e. an axis parallel with the ground of the treatment room. In various embodiments, including the embodiment shown in FIGS. 3a-c, the fixed axis 380 is perpendicular to a plane formed by the support structure 310. The fixed axis 380 passes through the rotation mechanism 320.

In FIG. 3a, the rotary actuators 321, 322 and 323 have been positioned so that the rotational axes of the first, second and third rotary actuators 321, 322 and 333 are aligned. The first wedge 324 and the second wedge 325 need not be identical, but in an example where the wedges are identical such that $\theta_1=\theta_2$ then the arrangement shown in FIG. 1 can be effected by actuating the rotary actuators 321, 322 and 333 such that the wedges 324, 325 are aligned oppositely. As the two wedges 324 and 325 have equal wedge angles and are precisely oppositely arranged, in other words so that the tilt which they impose is directed in opposing directions, the rotation mechanism 320 as a whole imparts no tilt to the gantry 330. In other words, the outer face of the first rotary actuator 321, or equivalently the plane defined by the support surface 310, is parallel with the inner face of the third rotary actuator 323. In other words, the 'outer' face of the rotation mechanism 320 is parallel with the 'inner' face of the rotation mechanism 320. While in a simple embodiment the wedges are identical, the skilled person will appreciate that such an arrangement can also be achieved with wedges which are not identical.

The radiation source is configured to emit radiation along a radiation axis 390. The radiation axis 390 makes an angle $\Phi$ with the fixed axis 380. The gantry rotation mechanism is configured to tilt the gantry in order to adjust, i.e. change, the angle $\Phi$ which the radiation axis 390 makes with the fixed axis 380. The fixed axis 380 is defined by the gantry rotation mechanism 320 and does not move in space. When the gantry rotation mechanism 320 orients the gantry 330 in the manner depicted in FIG. 3a, $\Phi$ is 90°, or substantially or approximately equal to 90°.

The orientation of the apparatus depicted in FIG. 3a is suitable for performing co-planar treatments. The radiation apparatus 300 may thus be configured to operate in a first mode of operation, which allows for co-planar treatments. With reference to FIG. 3a, as the rotation mechanism 320 rotates the gantry 330 about the fixed axis 380, e.g. as the first rotary actuator 321 is actuated, radiation emitted by the radiation source 332 can sweep out a circle. Radiation can be applied to the patient from a plurality of angles around the circle. The circle may be described as lying in a radiation plane. The radiation axis lies in the radiation plane. The radiation axis 390 makes an angle of 90° with respect to the fixed axis 380 independent of the degree to which the gantry is rotated about the fixed axis 380. In an example in which the radiation source is configured to direct radiation toward a detector 334 positioned diametrically opposite the radiation source 332 around the gantry 330, and both have a fixed position relative to one another, then the radiation plane is coincident with the gantry plane. The fixed rotation axis 380 is perpendicular with the radiation plane. In apparatus designed to have an isocentre, the fixed rotation axis 380 passes through the isocentre.

FIG. 3b shows the result when at least the second rotary actuator 322 is rotated by 180° with respect to the arrangement depicted in FIG. 3a, thereby placing the first and second wedges 324, 325 in the same orientation. A maximum tilt of a total angle of $\theta_1=\theta_2$ is then imposed between the inner and outer faces of the gantry rotation mechanism 320. FIG. 3c shows the first actuator 321 having been rotated by 180° with respect to the arrangement shown in FIG. 3b. In other words, the gantry rotation mechanism 320 has rotated the gantry 330 through 180° about the fixed axis 380.

A lesser tilt can be imposed by rotating the second rotary actuator 322 to different orientations, e.g. by less than 180°. As the second rotary actuator 322 is rotated by less than 180° with respect to either orientation shown in FIG. 3b or 3c, the two wedges 324, 325 are placed at an intermediate position between the fully 'cancelled-out' position of FIG. 3a and the maximal tilt orientations of FIGS. 3b and 3c. This means that the total angle of lean, or tilt, imposed by the gantry rotation mechanism 320 is somewhere between the minimum shown in FIG. 3a and the maximum shown in FIGS. 3b and 3c.

In this way, the amount as well as the direction of tilt imposed by the gantry rotation mechanism 320 can be controlled. It can be seen that rotation of the first rotary actuator 321 can be used to determine the direction in which that angle of tilt is pointing. The third rotary actuator 323 can be actuated to prevent the gantry from rotating about fixed axis 380 while the first or second rotary actuators 321, 322 are being actuated. This allows the degree of tilt of the gantry to be changed without imparting any rotation of the gantry about fixed axis 380.

In summary, by actuating the first rotary actuator 321, the gantry can be rotated about the fixed axis 380 which passes through the gantry rotation mechanism 320. In the absence of any actuation of the second and third rotary actuators 322, 323, actuation of the first rotary actuator thus causes the radiation source to rotate about the fixed axis 380. In other words, the gantry rotation mechanism 320 is configured to rotate the radiation source around the fixed axis 380. This allows radiation to be applied to a patient from multiple angles. By actuating the second rotary actuator 322, the relative orientation, i.e. alignment, of the first and second wedges 324, 325 can be adjusted. By adjusting the relative orientation of the two wedges 324, 325, the degree of tilt of the gantry 330 with respect to the fixed axis 380 can be adjusted. The degree of tilt is defined by the angle $\Phi$ which the radiation axis makes with the fixed axis 380. The degree of tilt can be adjusted between a minimal or 'zero-tilt' orientation, in which the angle $\Phi$ is 90° and a maximal degree of tilt. The maximal degree of tilt is defined by $\theta_1+\theta_2$, and in an apparatus configured and aligned in the manner shown in FIGS. 3a-c: $\theta_1+\theta_2=\Phi_{max}$. Adjusting the tilt angle also, equivalently, changes the angle between an outermost and an innermost surface of the gantry rotation mechanism 320. The third rotary actuator 323 can be actuated to compensate for the horizontal rotations imposed by the other two rotary actuators 321, 322. In this way, a gantry rotation mechanism 320 is provided which is coupled to the gantry 330 and is configured to rotate the gantry 330 about a fixed axis 380 which passes through the gantry rotation mechanism 320, and tilt the gantry 330 with respect to the fixed axis 380 to change an angle $\Phi$ which the radiation axis 390 makes with the fixed axis 380.

Thus, in addition to the first mode, the radiation treatment apparatus is configured to provide treatment in a second mode. In the second mode, the gantry is tilted with respect to the fixed axis 380. The radiation source 332 is also tilted, and thus the radiation axis 390 is moved to make a non-perpendicular angle with the fixed axis 380. Thus, non-coplanar treatment may be provided.

The gantry rotation mechanism 320 is communicatively coupled to a controller suitable for effecting respective and combined actuation of the rotary actuators. The controller may comprise, or be described as, a computing device or a processor; the controller may be any machine capable of executing a set of instructions (sequential or otherwise) that specify actions to be taken by the gantry rotation mechanism 320.

The rotary elements 321, 322, 333 may comprise any suitable actuator, for example each may comprise a torque motor, otherwise known as a rotary synchronous motor or a direct drive motor. Torque motors typically consist of a pair of concentric rings comprising an inner ring and an outer ring. On the outer circumferential surface of the inner ring there are a series of permanent magnets, and on the inner circumferential surface of the outer ring there is a coil unit. When power is provided to the coil unit it is energised so that the magnetic interaction between this and the permanent magnets causes a relative rotation to be imposed between the inner and outer rings. When the outer ring is mounted to a surface or otherwise fixed to a substrate, the inner ring will then be caused to rotate. In this way, a compact disc-shaped rotary actuator unit is obtained. Such devices are generally known to the skilled person and need not be discussed in further detail herein.

It will be understood that the above description of specific embodiments is by way of example only and is not intended to limit the scope of the present disclosure. Many modifications of the described embodiments, some of which are now described, are envisaged and intended to be within the scope of the present disclosure.

FIGS. 4a-c show a radiation treatment apparatus comprising a second embodiment of the gantry rotation mechanism. As with the first embodiment shown in FIGS. 3a-c, the apparatus depicted in FIGS. 4a-c comprises a support surface 410, a gantry rotation mechanism 420, and a gantry 430. The arrangement, configuration and operation of the various components is broadly similar to the components described in relation to FIGS. 3a-c unless explicitly noted herein and like reference numerals have been used to denote like components.

In the FIGS. 4a-c, the gantry rotation mechanism 420 comprises a hexapod, otherwise known as a Stewart platform or Gough-Stewart platform. The hexapod comprises a baseplate 421 and a top plate 422 which serve as the outer and inner faces of the gantry rotation mechanism 420. The top plate is moveable with respect to the base plate and may therefore be referred to as a moveable platform. The gantry 430 is coupled to the top plate 422 and the base plate 421 is coupled to the support structure 410. As with the arrangement shown in FIGS. 3a-c, in the arrangement shown in FIGS. 4a-c the gantry 430 is fixedly attached to the gantry rotation mechanism 420 and the gantry rotation mechanism 420 is fixedly attached to the support structure.

Six 'legs' 423-428 join the top plate 422 to the base plate 421. Each leg is able to change its effective length. This can be accomplished by the use of actuators, e.g. slideable actuators or 'sliders'. The legs 423-428 are longitudinally adjustable along their longitudinal axis, and may change their effective length for example through a telescopic movement. For example, each leg may comprise a prismatic joint configured to provide a linear sliding movement between two component parts of the leg in order to change the effective length of the leg. The legs may also be termed 'struts' or 'stays'. The legs may comprise hydraulic cylinders or electric spindles, which each extend between the base plate 421 and the top plate 422. The legs are attached in pairs to three regions on the inner surface of the baseplate 421, and cross over to be attached at three regions on the top plate 422 in a known manner.

The outer face of the baseplate 421 is fixed to the support structure 410. By changing the effective lengths of the legs 423-428, the position and orientation of the top-plate can be altered. The hexapod allows a combined translational and rotary movement along or about the six coordinates. Accordingly, gantry rotation mechanism 420 has six degrees of freedom. This allows the gantry rotation mechanism to move in the three 'linear movement' axes; with respect to FIGS. 4a-c these axes may be defined as an x-axis parallel with the fixed axis 480, a y axis that lies in the plane of the support surface 410, and a z-axis into the plane of the diagram. The hexapod also allows rotation/tilt about the three rotation co-ordinate axes; with respect to FIGS. 4a-c these may be defined as rotation about the fixed axis 480, and about two tilting axes which are both perpendicular to one another and to the fixed axis 480.

In a preferred implementation, the baseplate 421 is a rotary actuator of the form described in relation to the arrangement depicted in FIGS. 3a-c. Thus, rotation of the gantry about the fixed axis 480 may be effected in a simple and easy manner. In this implementation, the legs of the hexapod are fixed directly to the rotatable plate/rotor of the rotary actuator 421, and hence the entire hexapod can be rotated together with the gantry 430 about fixed axis 480.

FIG. 4b shows the result when the legs of the hexapod adjust their lengths so as to impart a tilt to the gantry 430. In a manner similar to that described with respect to the arrangement shown in FIG. 3b, a tilt angle of Φ is formed between the radiation axis and the horizontal axis 480. Equivalently, an angle Φ is formed between the top plate 422 and the fixed axis 480. FIG. 4c shows the rotary actuator 421 having been rotated by 180° with respect to the arrangement shown in FIG. 4b. In other words, the gantry rotation mechanism 420 has rotated the gantry 430 through 180° about the fixed axis 480. Accordingly, the direction of tilt has been rotated by 180°.

As will be appreciated, the legs 423-428 can be actuated to adjust the tilt angle Φ. As with the embodiment of FIG. 3a-c, the total angle of lean, or tilt, imposable by the gantry rotation mechanism 420 is somewhere between the minimum 'zero tilt' configuration shown in FIG. 4a and a maximum tilt angle defined by the maximal and minimal extendable lengths of legs 423-428.

In summary, by actuating the rotary actuator 421, the gantry can be rotated about the fixed axis 480 which passes through the gantry rotation mechanism 420. Actuation of the rotary actuator 421 thus causes the radiation source to rotate about the fixed axis 480. In other words, the gantry rotation mechanism 420 is configured to rotate the radiation source around the fixed axis 480. This allows radiation to be applied to a patient from multiple angles. By actuating the legs of the hexapod in a suitable manner, the relative orientation, i.e. alignment, of the baseplate/rotary actuator 421 and the top plate 422 can be adjusted. Accordingly, the degree of tilt of the gantry 430 with respect to the fixed axis 480 can be adjusted. In this way, a gantry rotation mechanism 420 is provided which is coupled to the gantry 430 and which is configured to rotate the gantry 430 about a fixed axis 480 which passes through the gantry rotation mechanism 420, and which is configured to tilt the gantry 430 with respect to the fixed axis 480 to change an angle CD which the radiation axis 490 makes with the fixed axis 480.

As with the first embodiment, the gantry rotation mechanism 420 of the second embodiment is communicatively coupled to a controller suitable for controlling and providing suitable signals to the gantry rotation mechanism 420. The controller is able to effect respective and combined actuation of the legs of the hexapod in order to provide the functionality disclosed herein.

Because the hexapod is configured to move the gantry in 6 dimensions/directions, the legs of the hexapod may be configured to position the gantry such that, no matter the tilt angle Φ, the radiation axis and fixed axis meet each other at the same fixed point in space. This point is the isocentre 485. The legs of the hexapod are controllable, in other words the hexapod is configured, to account for a change in the position of the isocentre which may otherwise occur as the gantry 430 is tilted by moving the gantry in a direction parallel with the baseplate of the hexapod, i.e. in a direction in a plane which is perpendicular to the fixed axis 480.

Figure 5A:
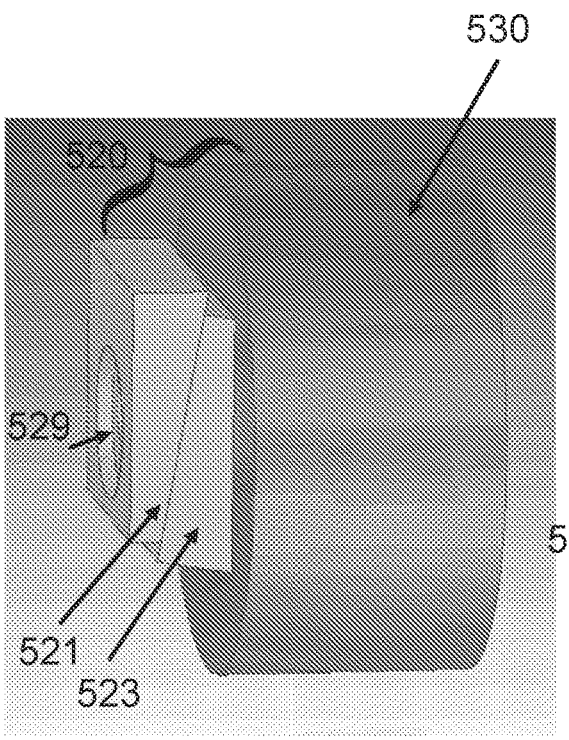
Figure 5B:
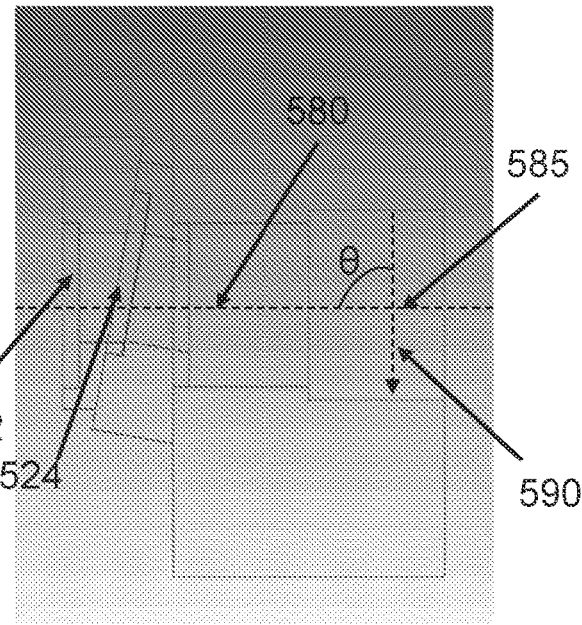
Figure 5C:
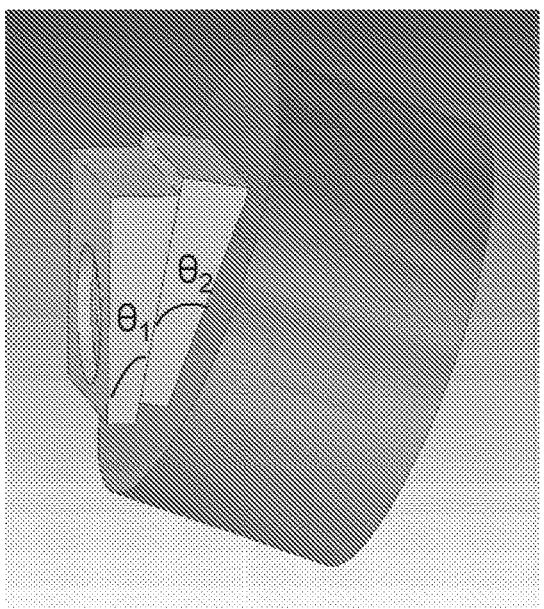
Figure 5D:
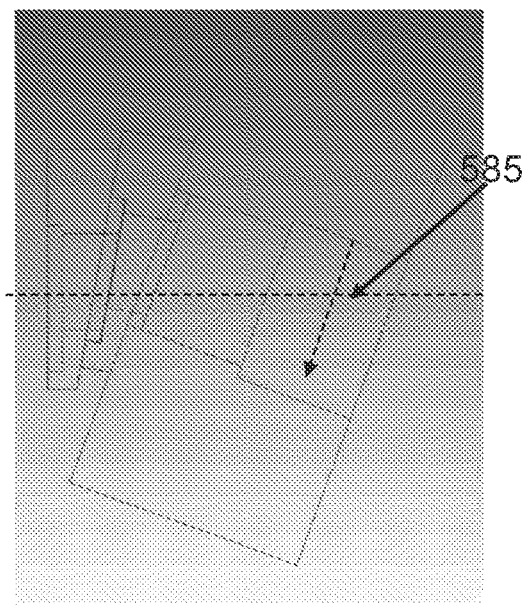

FIGS. 5a-d show a third embodiment of the present disclosure. In the third embodiment, the gantry rotation mechanism comprises two wedges or wedge elements 521, 523. The components of the third embodiment are structurally and functionally similar to the like components of the other embodiments described herein, unless stated otherwise herein. FIGS. 5a and 5b show the gantry rotation mechanism in its "zero tilt" state, i.e. in which the fixed axis 580 and the radiation axis 590 are perpendicular to one another. In this orientation, the device is suitable for operation in a first mode, i.e. the device is suitable for providing coplanar treatment. FIG. 5b is a cross-section of the device in the orientation depicted in FIG. 5a. FIGS. 5c and 5d show the apparatus at its maximum angular displacement, when the wedge angles of the first and second wedges 521 and 523 combine to tilt the gantry 530 with respect to the fixed axis.

FIG. 5c depicts the device when a relative rotation has been effected between the first and second wedge 521, 523 such that a tilt has been imparted to the gantry 530. The orientation of the device as depicted in FIG. 5c is suitable for providing non-coplanar treatment, i.e. the device is ready for operation in a second mode. FIG. 5d is a cross section of the device in the orientation depicted in FIG. 5c.

In the third embodiment, the gantry rotation mechanism 520 comprises a first wedge 521 and In a second wedge 523 each comprising rotation means, e.g. respective rotary actuators 522 and 524. The first wedge 521 is coupled to a support structure (not shown) which is similar in form and function as the previously described support structures. The first wedge may be directly coupled to the support structure, and may be rotationally coupled with the support structure. In other words, the first wedge 521 is configured to rotate with respect to the support structure. The gantry rotation mechanism is positioned in-between the support structure and the gantry. The radiotherapy device 500 comprises a first rotary actuator 522 configured to rotate the gantry 530 about the fixed axis 580. The first rotary actuator 522 may be comprised within the first wedge 521. The first rotary actuator 522 is configured to rotate the first wedge 521 which, in the absence of other relative rotation, i.e. when the first and second wedges 521, 523 and gantry 530 maintain fixed relationship with respect to one another, causes the gantry 530 to rotate about the fixed axis 580.

The first wedge 521 is coupled to the second wedge 523. The two wedges 521, 523 are rotationally coupled to one another. The second wedge 523 is coupled to the gantry 530, and may be fixedly attached to the gantry 530. The radiotherapy apparatus 500, and specifically the second wedge 523, comprises a second rotary actuator 524 configured to effect relative rotation between the first and second wedge 521, 523. In other words, the second rotary actuator 524 is configured to rotate the second wedge 523 such that the relative orientation of the first and second wedge 521 and 523 changes such that a tilt is imparted to the gantry 530. Rotation of the second wedge causes the gantry 530 to tilt with respect to the fixed axis 580 such that the angle Φ which the radiation axis 590 makes with the fixed axis 580 changes. The angle which the fixed axis 580 makes with the radiation axis 590 is therefore adjustable by actuation of the gantry rotation mechanism 520.

The first rotary actuator 522 is configured to effect rotation around the fixed rotation axis 580, and the second rotary actuator 524 is configured to effect rotation around a second rotation axis. These rotation axes are different and are non-parallel and non-perpendicular to one another. The axes meet at an angle which defines the maximal tilt angle Φ of the gantry 530. Effecting rotation of the first rotary actuator 522 causes the second wedge 523 and the entire gantry 530, including the radiation source and imager (not shown) to rotate about the fixed axis 580. Effecting rotation of the second rotary actuator 524 causes the gantry to rotate about the axis of rotation of the second rotary actuator 524. Because the axes of rotation of to the first and second wedge 521, 523 are tilted with respect to one another, and because the second wedge 523 is coupled to the gantry 530, rotation of the second rotary actuator 524 causes the gantry 530 to tilt with respect to the fixed axis 580 in the manner described elsewhere herein. The rotary actuators 522, 524 may be of similar form and function to those described elsewhere herein.

The fixed axis 580 may be a horizontal axis, i.e. an axis parallel with the ground of the treatment room. In the embodiment shown in FIGS. 5*a-d* the fixed axis 580 is perpendicular to a plane formed by a support structure not shown in FIG. 5*a* that is similar to the support structures, such as support structure 310, described above. The fixed axis 580 passes through the rotation mechanism 520, and more specifically passes through the centre of rotation of the first rotary actuator 522.

In FIGS. 5*a-d*, the wedges 521 and 523 are offset with respect to one another. In the FIGS. 5*a-d*, the wedges are offset from one another, along a plane defined by the inner surface of the firs wedge 521 surface. In other words, the first and second wedges 521, 523 are offset in a plane defined by the angled face of the first wedge. The centre of rotation of the second rotary actuator 524 does not lie on the fixed axis 580. The uppermost and lowermost surfaces of the second wedge 523 do not align with the uppermost and lowermost surfaces of the first wedge 521.

The gantry rotation mechanism 520 of FIGS. 5*a-d* has at least two configurations/orientations: a first in which the plane of the gantry 530 is perpendicular to the fixed axis 580 (FIGS. 5*a*, 5*b*) and a second in which a maximal tilt angle is applied to the gantry 530 (FIGS. 5*c*, 5*d*). In both the first and second configurations, the first and second wedge 521, 523 are offset from one another such that the radiation axis 590 meets the fixed axis 580 at the same point in both the first and the second configurations. This point is the isocentre 585. In other words, the isocentre 585 can be made to lie at the same point in space for both the first configuration and the second configuration by arranging the wedges to be offset by a certain degree. The offset accounts for the change in the position of the point where the fixed axis and radiation axis meet which would otherwise occur if the offset weren't present. In the absence of the offset, in the second configuration the point where the radiation axis 590 meets the fixed axis 580 would map out a circle as the gantry is rotated about the fixed axis 580. This would mean the radiation device 500 would be unsuitable for most radiotherapy treatments without additional and complex hardware such as a patient support surface which moves within the bore of the radiation device as the gantry 530 is rotated. A radiotherapy device comprising a gantry rotation mechanism 520 with offset wedges 521, 523 in the manner described can provide both co-planar and non-coplanar treatment in two respective configurations, wherein the position of the isocentre is unchanged between the first and second configuration. This is advantageous because it means that radiation can be directed at a target region in a patient from a variety of angles without the need for complex and expensive patient positioning equipment, in fact without the need to move the patient at all.

The first wedge 521 has a wedge angle $\theta_1$ and the second wedge 523 has a wedge angle $\theta_2$. The maximal tilt angle $\Phi_{max} = \theta_1 + \theta_2$. As with the wedges described with respect to the first embodiment, the wedges 521, 523 need not be identical and may each have a different wedge angle. In an example where the wedges are identical such that $\theta_1 = \theta_2$, then the arrangement shown in FIGS. 5*a*, 5*b* in which there is zero tilt can be effected by actuating the second rotary actuator 524 such that the wedges 521, 523 are aligned oppositely. In other words, such that wedge angles $\theta_1$ and $\theta_2$ are pointing in opposite directions. In this configuration of the gantry rotation mechanism 520, the rotation mechanism as a whole imparts no tilt to the gantry. In other words, the outer face of the first wedge 521, or equivalently the plane defined by the support surface, is parallel with the inner face of the second wedge 523. The offset wedge arrangement shown in FIGS. 5*a-d* provides an arrangement in which the isocentre is in the same position when the wedges are aligned (FIGS. 5*c*, 5*d*) and when the wedges are out of alignment (FIGS. 5*a*, 5*b*).

In another embodiment similar to that shown in FIGS. 5*a-d*, the radiation treatment apparatus comprises a gantry rotation mechanism which comprises a single wedge element. As with the other embodiments, the gantry rotation mechanism is positioned in-between a support structure and the gantry, however the rotation mechanism is comprised of a wedge element with a single wedge angle. The wedge element can take a variety of forms, however one form may be similar to that depicted in FIGS. 5*a-d* but wherein no relative rotation is possible between the first wedge and the second wedge such that the two wedges from a single wedge element. In such a radiotherapy apparatus, co-planar treatment may be performed. Such a device would be relatively cheap and easier to manufacture. As with the other embodiments, the gantry rotation mechanism is configured to rotate the gantry about a fixed axis which passes through the gantry rotation mechanism, however in this embodiment the gantry is permanently tilted with respect to the fixed axis by an angle defined by the angle of the wedge element. The wedge element may be shaped such that it can be described as being formed of two offset, integral wedges. This would provide a radiotherapy device with an isocentre which doesn't move position as the gantry is rotated.

It will be appreciated that the apparatus of the present disclosure allows both coplanar and non-coplanar treatment and thus the number of options available to a clinician during the treatment planning stage is increased. Non-coplanar treatment allows a more conformal dose distribution to a target region.

The present apparatus has excellent stability. This is in part because the gantry is rotatable, and in particular because the gantry is a ring gantry. Typically, ring gantries are more stable than C-arm type gantries but provide fewer options in terms of angles from which radiation can be applied to a patient. In contrast, the present application is a ring gantry, providing the associated stability, but also provides an increased range of angles from which radiation can be applied to a patient.

FIG. 6 illustrates a block diagram of an example machine 600 upon which any one or more of the techniques (e.g., methodologies) discussed herein may perform. Examples, as described herein, may include, or may operate by, logic or a number of components, or mechanisms in the machine 600. Circuitry (e.g., processing circuitry) is a collection of circuits implemented in tangible entities of the machine 600 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 600 follow.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 600 may include a hardware processor 602 (e.g., a central processing unit (CPU), a graphics processing unit (GPU), a hardware processor core, or any combination thereof), a main memory 604, a static memory (e.g., memory or storage for firmware, microcode, a basic-input-output (BIOS), unified extensible firmware interface (UEFI), etc.) 606, and mass storage 608 (e.g., hard drive, tape drive, flash storage, or other block devices) some or all of which may communicate with each other via an interlink (e.g., bus) 630. The machine 600 may further include a display unit 610, an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 608, a signal generation device 618 (e.g., a speaker), a network interface device 620, and one or more sensors 616, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 602, the main memory 604, the static memory 606, or the mass storage 608 may be, or include, a machine readable medium 622 on which is stored one or more sets of data structures or instructions 624 (e.g., software) embodying or utilized by any one or more of the techniques or functions described herein. The instructions 624 may also reside, completely or at least partially, within any of registers of the processor 602, the main memory 604, the static memory 606, or the mass storage 608 during execution thereof by the machine 600. In an example, one or any combination of the hardware processor 602, the main memory 604, the static memory 606, or the mass storage 608 may constitute the machine readable media 622. While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include a non-transitory medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices magnetic disks, such as internal hard disks and removable disks; magneto-optical disks; and CD-ROM and DVD-ROM disks.

The instructions 624 may be further transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software. A transmission medium is a machine readable medium.

The processor 602 of machine 600 can include instructions 624 which cause the processor 602 to implement the methods described herein. Specifically, the processor 602 can perform instructions such as to generate one or more control signals that can be provided to one or more actuators such as to cause the radiation source to emit radiation along a radiation axis, position the gantry rotation mechanism between the support structure and the gantry, rotate the gantry about a gantry rotation axis, and tilt the gantry with respect to the gantry rotation axis such that the radiation axis is non-perpendicular with the gantry rotation axis.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A radiotherapy apparatus comprising:
a gantry rotation mechanism configured to be positioned between a support structure and a gantry, the gantry comprising a source of radiation attached to the gantry and configured to emit radiation along a radiation axis, wherein the gantry rotation mechanism comprises at least a first rotatable wedge and a second rotatable wedge each comprising a rotary actuator, and wherein the gantry rotation mechanism is configured to:
rotate the gantry about a gantry rotation axis; and
tilt the gantry with respect to the gantry rotation axis by effecting relative rotation of the first and second rotatable wedges to define at least a first configuration and a second configuration wherein, in the first configuration, the radiation axis is perpendicular with the gantry rotation axis, wherein in the second configuration, the radiation axis is non-perpendicular with the gantry rotation axis, wherein the first rotatable wedge and the second rotatable wedge are offset from one another such that, in both the first configuration and the second configuration, the radiation axis and the gantry rotation axis meet at a same point in space to define an isocentre that is common to both the first configuration and the second configuration, and wherein the offset results in a center of rotation of the second rotatable wedge that does not lie on a rotation axis of the first wedge.

2. The radiotherapy apparatus of claim 1, further comprising:
the gantry;
the source of radiation attached to the gantry and configured to emit radiation along the radiation axis; and
the support structure for supporting the gantry.

3. The radiotherapy apparatus of claim 2, wherein the gantry rotation axis passes through the gantry rotation mechanism, and wherein the gantry rotation axis is a fixed axis that is fixed with respect to the support structure.

4. The radiotherapy apparatus of claim 2, wherein the radiation source is fixedly attached to the gantry.

5. The radiotherapy apparatus of claim 2, further comprising at least one of an imaging apparatus and a beam stop attached to the gantry, the at least one of the imaging apparatus and the beam stop being positioned diametrically opposite the radiation source such that the radiation axis passes through the at least one of the imaging apparatus and the beam stop.

6. The radiotherapy apparatus of claim 2, further comprising a patient support surface positioned such that a patient positioned on the patient support surface is capable of being positioned along the gantry rotation axis.

7. The radiotherapy apparatus of claim 2, wherein the support structure supports the gantry and the gantry rotation mechanism.

8. The radiotherapy apparatus of claim 2, wherein the gantry rotation mechanism is further configured to tilt the gantry to adjust an angle which the radiation axis makes with the gantry rotation axis.

9. The radiotherapy apparatus of claim 2, wherein the gantry rotation mechanism comprises a rotatable actuator and a hexapod, said hexapod comprising a first platform and a second platform, the first platform being coupled with the rotatable actuator and the second platform being coupled with the gantry, wherein the rotatable actuator is configured to rotate the gantry about the gantry rotation axis.

10. The radiotherapy apparatus of claim 2, wherein the gantry rotation mechanism comprises at least one of:
   a hexapod; or
   a wedge element.

11. A method of manufacturing a radiotherapy apparatus for delivering radiation to a patient, comprising:
   providing a gantry;
   providing a source of radiation attached to the gantry, the radiation source being configured to emit radiation along a radiation axis;
   providing a support structure for supporting the gantry; and
   positioning a gantry rotation mechanism between the support structure and the gantry, wherein the gantry rotation mechanism comprises at least a first rotatable wedge and a second rotatable wedge each comprising a rotary actuator, and wherein the gantry rotation mechanism is configured to:
      rotate the gantry about a gantry rotation axis; and tit the gantry with respect to the gantry rotation axis by effecting relative rotation of the first and second rotatable wedges to define at least a first configuration and a second configuration, wherein, in the first configuration, the radiation axis is perpendicular with the gantry rotation axis wherein in the second configuration, the radiation axis is non-perpendicular with the gantry rotation axis, wherein the first rotatable wedge and the second rotatable wedge are offset from one another such that, in both the first configuration and the second configuration, the radiation axis and the gantry rotation axis meet at a same point in space to define an isocentre that is common to both the first configuration and the second configuration, and wherein the offset results in a center of rotation of the second rotatable wedge that does not lie on a rotation axis of the first wedge.

12. A method of adjusting a configuration of a radiotherapy device, the radiotherapy device for delivering radiation to a patient, the device comprising:
   a gantry; a source of radiation attached to the gantry and configured to emit radiation along a radiation axis;
   a support structure for supporting the gantry; and
   a gantry rotation mechanism positioned between the support structure and the gantry,
   wherein the gantry rotation mechanism is configured to rotate the gantry about a gantry rotation axis and tilt the gantry with respect to the gantry rotation axis such that the radiation axis is non-perpendicular with the gantry rotation axis, and wherein the gantry rotation mechanism comprises at least a first rotatable wedge and a second rotatable wedge each comprising a rotary actuator;
   the method comprising:
      tilting the gantry into a first configuration in which the radiation axis is perpendicular with the gantry rotation axis; and
      tilting the gantry into a second configuration by effecting relative rotation of the first and second rotatable wedges, in which the radiation axis is non-perpendicular with the gantry rotation axis;
      wherein the first rotatable wedge and the second rotatable wedge are offset from one another such that, in both the first configuration and the second configuration, the radiation axis and the gantry rotation axis meet at a same point in space to define an isocentre that is common to both the first configuration and the second configuration, and wherein the offset results in a center of rotation of the second rotatable wedge that does not lie on a rotation axis of the first wedge.

13. A non-transitory computer readable medium comprising computer-executable instructions which, when executed by a processor, cause the processor to control a gantry rotation mechanism to perform the method of claim 12.

* * * * *